United States Patent
Haugland et al.

(10) Patent No.: US 7,574,262 B2
(45) Date of Patent: Aug. 11, 2009

(54) TRANSMITTER OR RECEIVER MOUNTING

(75) Inventors: Morten Haugland, Aalborg (DK); Morten Hansen, Santa Clarita, CA (US)

(73) Assignee: Neurodan A/S, Aalborg (DK)

( * ) Notice: Subject to any disclaimer, the term of this patent is extended or adjusted under 35 U.S.C. 154(b) by 1005 days.

(21) Appl. No.: 10/465,798

(22) Filed: Jun. 20, 2003

(65) Prior Publication Data
US 2004/0015208 A1    Jan. 22, 2004

(30) Foreign Application Priority Data
Jun. 21, 2002    (GB)    ................... 0214439.2

(51) Int. Cl.
*A61N 1/18* (2006.01)
(52) U.S. Cl. ........................................ 607/49
(58) Field of Classification Search ............ 607/49, 607/48, 60, 144, 149, 155, 156, 30, 32, 33; 128/903; 343/718, 878, 908
See application file for complete search history.

(56) References Cited

U.S. PATENT DOCUMENTS

| | | | | |
|---|---|---|---|---|
| 5,109,845 A | * | 5/1992 | Yuuchi et al. ................. | 607/60 |
| 5,545,191 A | * | 8/1996 | Mann et al. ................... | 607/57 |
| 5,862,803 A | * | 1/1999 | Besson et al. ................ | 600/508 |
| 6,441,747 B1 | * | 8/2002 | Khair et al. ............ | 340/870.16 |
| 6,788,976 B2 | * | 9/2004 | Gesotti ........................ | 607/49 |
| 2001/0053674 A1 | * | 12/2001 | Katoh ......................... | 455/90 |

FOREIGN PATENT DOCUMENTS

WO    WO 01/60445 A2    8/2001

OTHER PUBLICATIONS

Merriam-Webster Online, (http://webster.com), defined: flange.*

* cited by examiner

*Primary Examiner*—George R Evanisko
*Assistant Examiner*—Alyssa M Alter
(74) *Attorney, Agent, or Firm*—Pillsbury Winthrop Shaw Pittman, LLP

(57) ABSTRACT

A mounting for fixing a transmitter or receiver to a surface comprises a mounting pad and a transmitter or receiver housing, the mounting pad having a face for applying to the surface and an opposite face and being provided with a first mating component of a rotatable connection and the transmitter or receiver housing having a second cooperating mating component of the rotatable connection, whereby the two components are mateable to mount the transmitter or receiver housing rotatably on the opposite face of the mounting pad.

16 Claims, 4 Drawing Sheets

TRANSMITTER OR RECEIVER MOUNTING

BACKGROUND OF THE INVENTION

1. Field of the Invention

The present invention relates to a mounting for a transmitter or a receiver, in particular to a mounting for a magnetic or aerial coil. Mountings in accordance with preferred embodiments of the invention may be useful in devices used to stimulate muscles in the human body, for example devices used in the treatment of foot-drop.

2. Description of the Related Art

Many patients who have suffered a stroke or other conditions, for example dorsiflexor injuries, peripheral nerve injuries, neuropathies, drug toxicities or diabetes, suffer from foot-drop. Foot-drop (or dropfoot) is an inability to lift the front of the foot (dorsiflexion), making it difficult to swing the leg forward in walking. Foot-drop caused by damage to the central nervous system (rather than to the peripheral nerve which controls the lower leg dorsiflexor muscles) can be alleviated by electrically stimulating the peroneal nerve, causing the lower leg dorsiflexor muscles to contract. Stimulation may be caused through the skin (transcutaneous stimulation) or via an implanted stimulator (subcutaneous stimulation). To cause contraction of the dorsiflexor muscles during the swing phase of gait only, a sensor is used to detect this phase. The sensor is typically a switch located under the heel inside the shoe. The switch is connected to an electrical stimulator on or under the surface of the leg.

A conventional unit for the treatment of foot-drop comprises a heel sensor, a controller and an electrical stimulator. The heel sensor, the controller and the electrical stimulator are connected by wires.

The present inventors have described in an earlier published patent application (WO01/60445) a unit for the treatment of foot-drop wherein the heel sensor and electrical stimulator communicate via a radio transmitter and receiver. In a preferred embodiment, an implanted multi-channel stimulator activates foot lift by stimulating the common peroneal nerve above the knee. The stimulation activates the dorsiflexors which lift the foot. The stimulating electrode is located under the skin just above the knee while the stimulator is located under the skin on the thigh. The stimulating electrode and stimulator are implanted by surgery under local anaesthesia. The implanted stimulator is controlled by an external control unit. The control unit transmits energy and control signals into the stimulator using a wired connection to a lightweight transmitting coil located on the skin over the implanted stimulator. The stimulation is activated by a wireless heel switch located in the shoe. The multiple channels of stimulation make it possible for the clinician to adjust the movement of the foot to ensure a balanced foot lift even when the device has been implanted for a period of time.

In devices such as this, the transmitting coil must be mounted on the skin. This can be achieved using an adhesive Velcro® pad which is attached to the skin, to which the transmitting coil is mounted using a cooperating Velcro® pad.

SUMMARY OF THE INVENTION

In a first aspect, the present invention relates to a mounting for fixing a transmitter or receiver to a surface, the mounting comprising a mounting pad and a transmitter or receiver housing, the mounting pad having a face for applying to the surface and an opposite face and being provided with a first mating component of a rotatable connection and the transmitter or receiver housing having a second cooperating mating component of the rotatable connection, whereby the two components are mateable to mount the transmitter or receiver housing rotatably on the opposite face of the mounting pad.

Preferably, the transmitter or receiver housing is a transmitting or receiving antenna housing. More preferably, the transmitting or receiving antenna housing is a transmitting or receiving coil housing. Highly preferably, the transmitting or receiving coil housing is a magnetic coil housing or an aerial coil housing.

In a preferred embodiment, the face of the mounting pad for applying to the surface is an adhesive face. Alternatively, the mounting pad may be provided with adhesive tape extending beyond the edge of the mounting pad for fixing the mounting pad to the surface. An adhesive surface of the adhesive tape may be applied to the opposite face of the mounting pad from the face for applying to the surface, such that the adhesive fixes the adhesive tape to the mounting pad in addition to fixing the adhesive tape to the surface. Alternatively, a non-adhesive surface of the adhesive tape may be applied to the face of the mounting pad for applying to the surface. In this case, the adhesive fixes the adhesive tape to the surface only. The adhesive tape must be fixed to the mounting pad by welding or by additional adhesive.

Preferably, the transmitter or receiver housing is in the form of a dish and the mounting pad is in the form of a plate, such that when the two components are mated the mounting pad sits at least substantially within the transmitter or receiver housing.

Preferably, one of the first and second mating components is a flanged boss and the other of the first and second mating components is a cooperating hole. More preferably, the cooperating hole has a first portion through which the flanged boss can pass and a second portion within which the flanged boss can sit but through which the flanged boss cannot pass. Highly preferably, the first portion and the second portion of the cooperating hole are divided by a flexible waist through which the flanged boss can be urged.

Preferably, the mounting is suitable for mounting to the human or animal body, in particular the mounting preferably has suitable size and weight for mounting to the human or animal body. Preferably, the mounting has a diameter of 10 cm or less, for example 5 cm or less, and a thickness of 2 cm or less. Preferably, the mounting has a weight of 50 g or less, more preferably 25 g or less.

Preferably, if the mounting is provided with adhesive as described above, the adhesive used is non-toxic.

In a second aspect, the present invention relates to a transmitter or receiver housing, constituting one component of a mounting as described above.

In a third aspect, the present invention relates to a mounting pad, constituting one component of a mounting as described above.

In a fourth aspect, the present invention relates to an electrical stimulation unit comprising a sensor, a transmitter, a transmitter mounting as described above and a stimulator, wherein the sensor controls the transmitter to transmit a signal to the stimulator.

Preferably, the sensor controls the transmitter by means of a controller.

The electrical stimulation unit may be intended for the treatment of foot-drop, in which case the sensor may be a pressure sensor for placing on the heel and the stimulator may be a stimulator for the peroneal nerve.

In a fifth aspect, the present invention relates to the use of a mounting as described above in mounting a transmitter or receiver on the human or animal body.

In a sixth aspect, the present invention relates to a method of producing nerve stimulation using an electrical stimulation unit as described above, comprising the steps of:

the sensor detecting a stimulus;
the sensor transmitting a signal to the controller;
the controller controlling the transmitter to transmit a signal to the stimulator; and
the stimulator producing nerve stimulation.

BRIEF DESCRIPTION OF THE DRAWINGS

The invention will now be described with reference to a preferred embodiment as illustrated in the accompanying drawings, in which.

DETAILED DESCRIPTION

Figure 1:
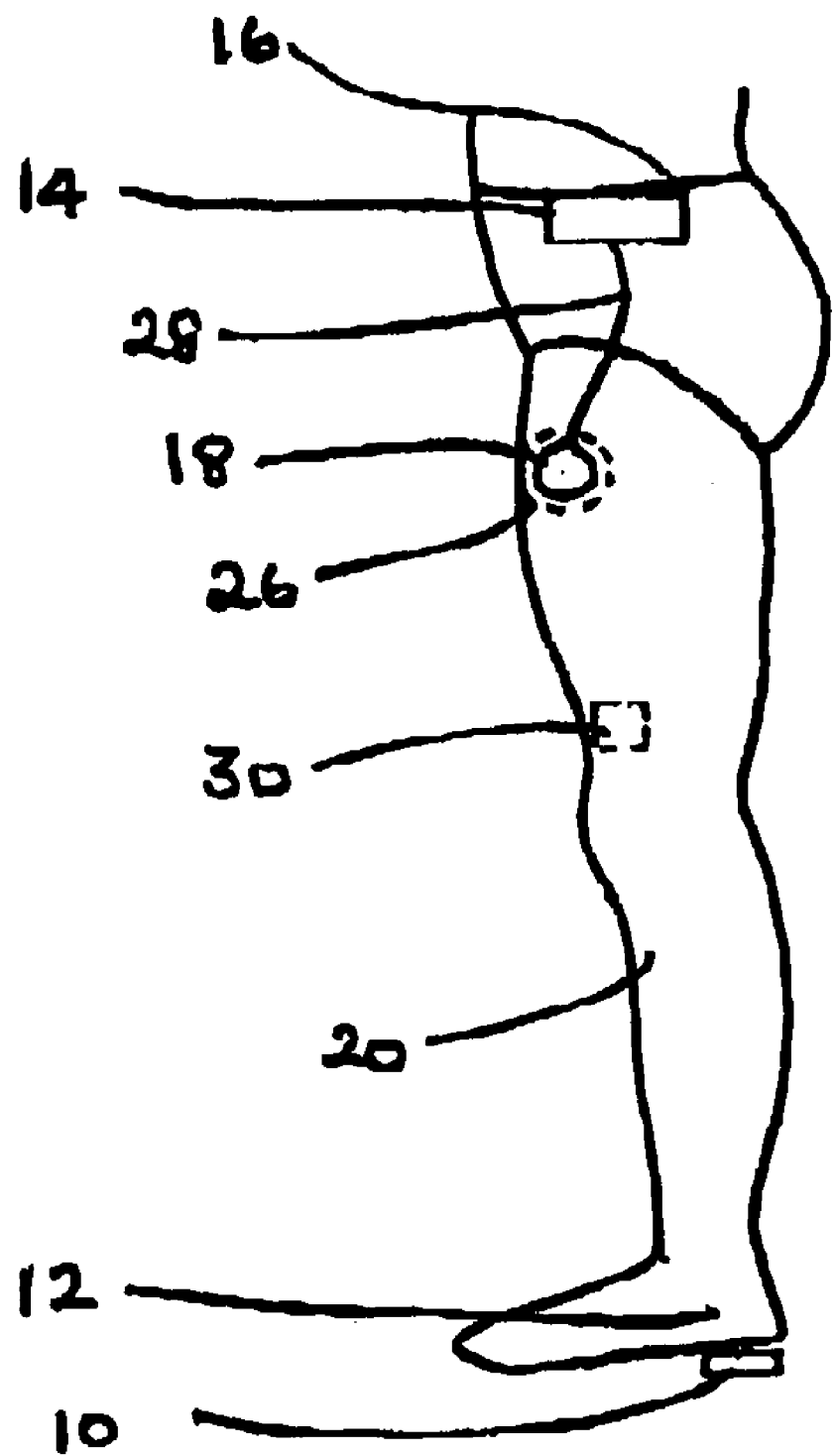
FIG. 1 shows schematically a foot-drop treatment unit of the invention.
Figure 2:
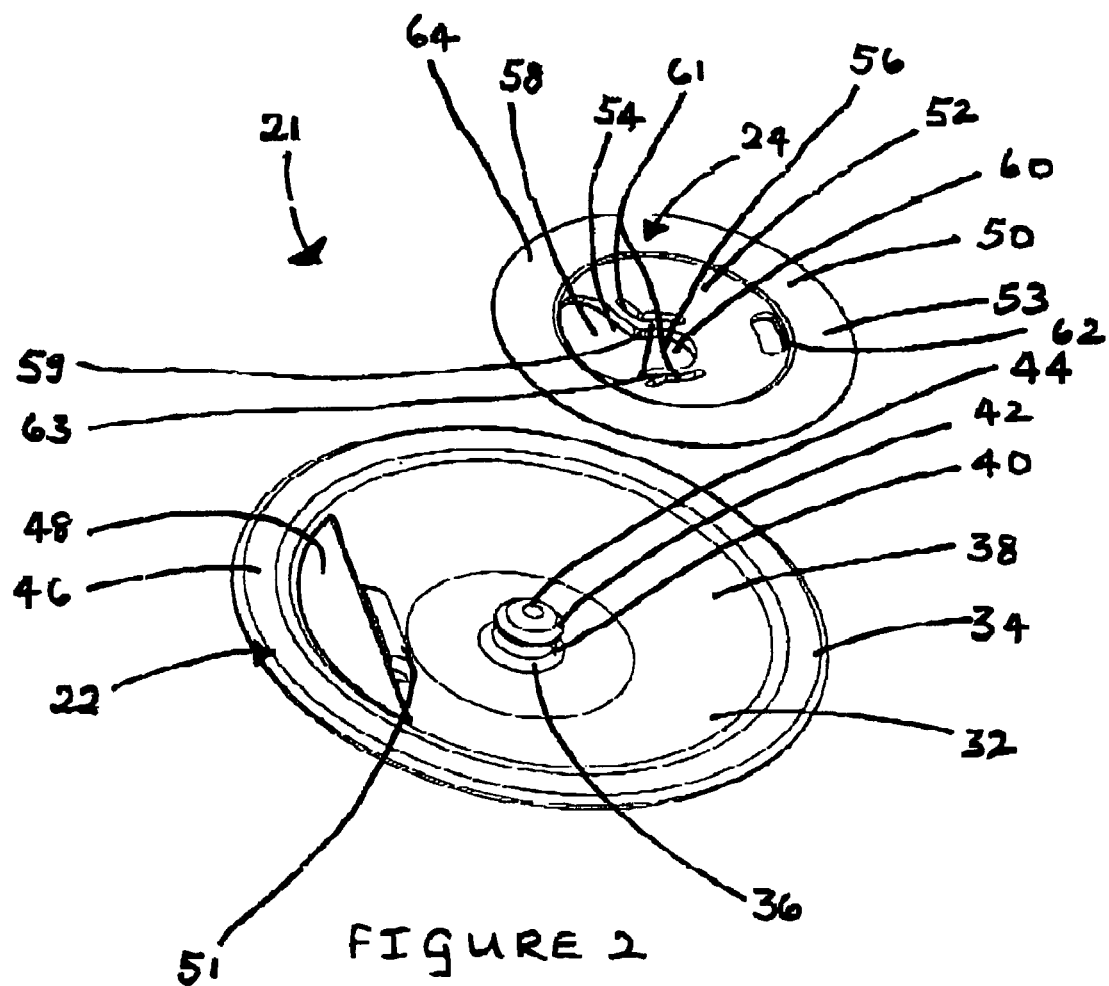
FIG. 2 shows a perspective view of the separated mounting pad and transmitting coil housing of the invention.

In the foot-drop treatment unit shown in FIG. 1, a heel sensor 10 is placed under the heel 12 of the patient. A control unit 14, which communicates with the heel sensor 10 via a radio link (not shown), is attached to the belt 16 of the patient. A magnetic transmitting coil 18 is mounted on the skin of the leg 20 of the patient on the thigh using a mounting 21 (FIG. 2) comprising a transmitting coil housing 22 and mating mounting pad 24 as described below. The magnetic transmitting coil 18 is positioned over a stimulator 26 positioned under the skin of the leg 20 of the patient and communicates with the stimulator 26 by a magnetic signal (not shown). The magnetic transmitting coil is connected to the control unit 14 by a wire 28. The stimulator 26 is connected by an implanted wire (not shown) to a stimulation electrode 30, positioned under the skin of the leg 20 of the patient above the knee.

The mounting 21 (FIG. 2) comprises a plastics transmitting coil housing 22 and a plastics mating mounting pad 24. The transmitting coil housing 22 has the form of a circular dish 32 provided with a lateral rim 34. The centre 36 of the concave surface 38 of the dish 32 is provided with a cylindrical boss 40 having a flange 42 around its distal end 44. At one side 46 of the dish 32 a plate 48 having the form of a circle segment is mounted parallel to the lateral rim 34. Within the dish 32 under the plate 48 the transmitting coil 18 is mounted. The wire 28 passes through a hole (not shown) in the dish 32. The wire 28 runs across the concave surface 38 of the dish through a conduit 51 and is attached to the transmitting coil 18 under the plate 48.

Figure 4:
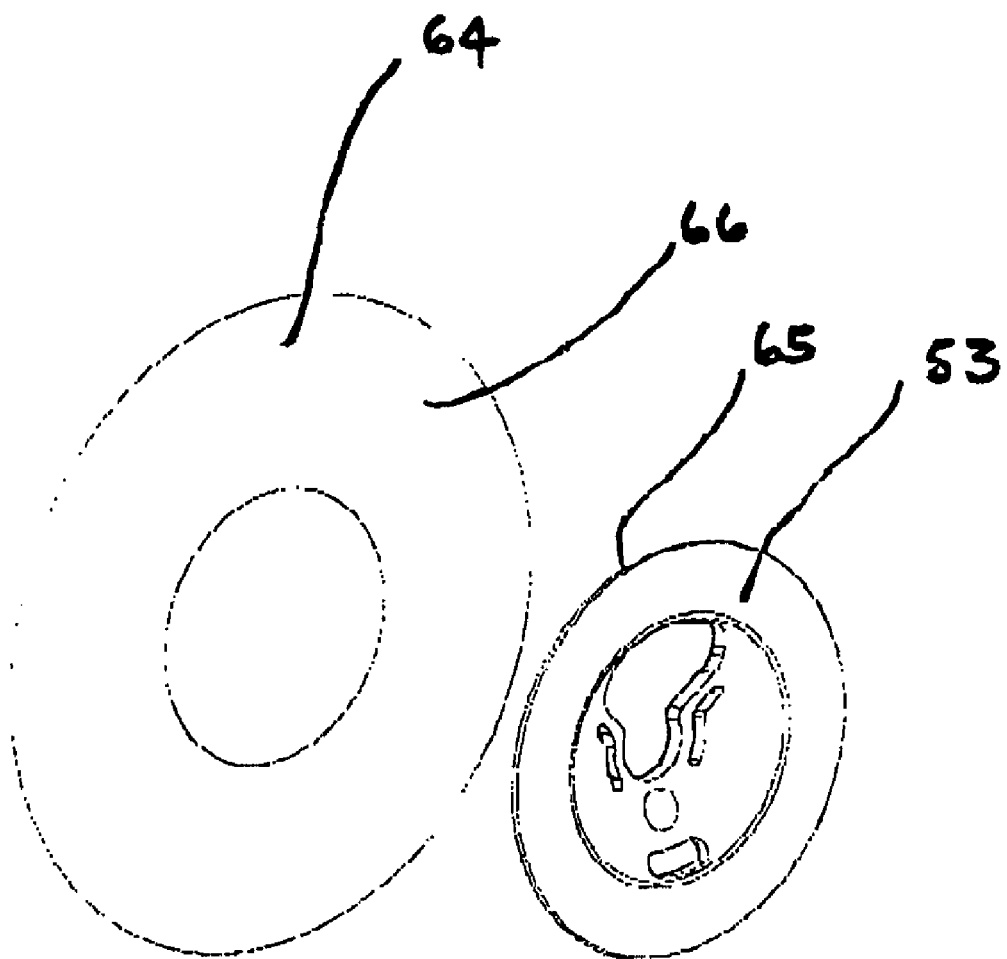
FIG. 4 shows a perspective view of the mating mounting pad of the invention and means for mounting the mated mounting pad to a patient.

The mating mounting pad 24 has the form of a circular plate 50 with a depressed circular central region 52 surrounded by a rim 53. The diameter of the circular plate 50 is smaller than the diameter of the transmitting coil housing dish 32. A hole 54 in the depressed region 52 has the form of a circle 56 joined to the longer side of an ellipse 58 via a waist 59. The circle 56 is centred on the centre 60 of the depressed region 52. Slots 61 are located in the depressed region 52 separated from each side of the waist 59 by strips 63 and following the shape of the waist 59. The depressed region 52 is provided with a further hole 62. To the lower surface 65 of the rim 53 of the circular plate 50 is applied the adhesive surface 66 of an annular single sided adhesive tape 64 (FIG. 4) which extends beyond the rim 53. Part of the adhesive surface 66 serves to attach the adhesive tape 64 to the surface 65. The part of the adhesive surface 66 extending beyond the rim 53 is covered with a release tape (not shown). Alternatively, the rim 53 may be attached to the back of the adhesive tape 64, such that the entire adhesive surface 66 of the adhesive tape 64 can be used to mount the mating mounting pad 24 to the patient.

In use, the release tape (not shown) is removed from the adhesive tape 64 of the mating mounting pad 24. The adhesive surface 66 of the adhesive tape 64 is applied to the leg 20 of the patient at the thigh directly above the stimulator 26, to attach the mated mounting pad 24 to the leg 20. In an alternative embodiment, the upper surface of the rim 53 of the mated mounting plate 24 is provided with adhesive, for example double sided adhesive tape, and the annular adhesive tape 64 is not used. The mating mounting pad 24 will remain on the leg 20 of the patient for several days until the adhesive (not shown) is dissolved by bathing or showering.

Figure 3:
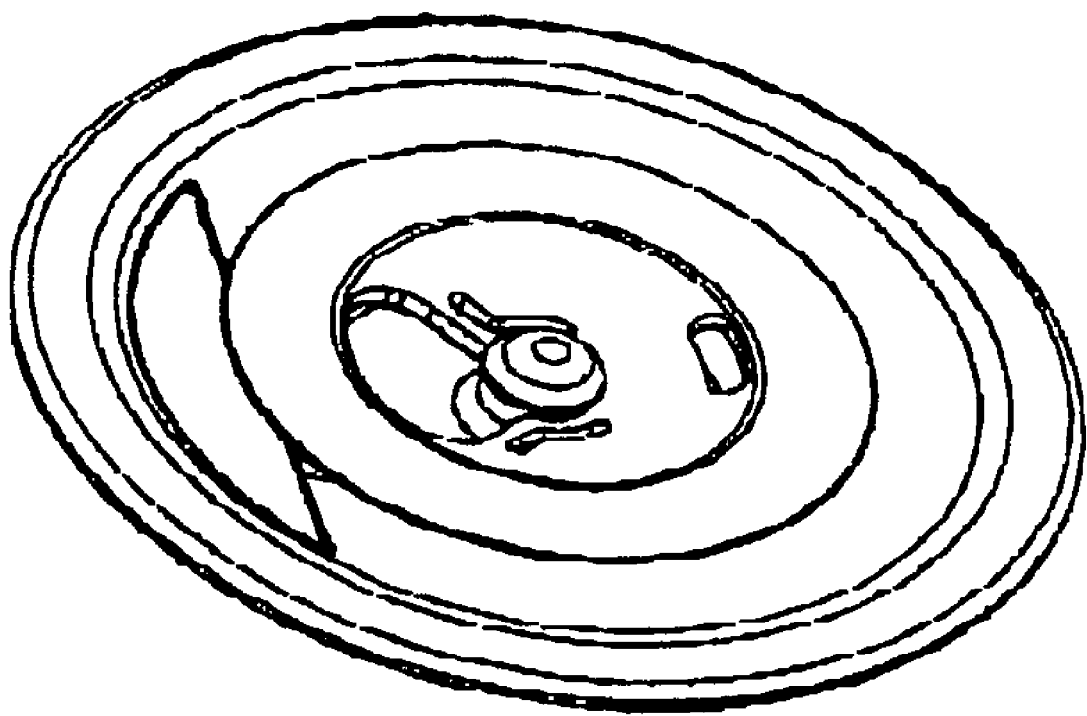
FIG. 3 shows a perspective view of the mating mounting pad and transmitting coil housing of the invention.

When the patient wishes to use the foot-drop treatment unit, the transmitting coil housing 22 is mounted to the mating mounting pad 24. This is done by applying the concave surface 38 of the dish 32 to the mating mounting pad 24 such that the boss 40 passes through the hole 54 of the mating mounting pad 24 at the ellipse 58. Lateral sliding of the transmitting coil 22 relative to the mating mounting pad 24 forces the boss 40 against the strips 63. The strips 63 deform by movement into the slots 61, widening the waist 59. This allows the boss 40 to click through the waist 59 such that the centre 36 of the dish 32 is aligned with the centre 60 of the depressed region 52 and the boss 40 sits within the hole 54 at the circle 56 of smaller diameter, with the mating mounting pad 24 within the dish 32 (FIG. 3). The diameter of the flange 42 of the boss 40 is such that the boss 40 cannot pass back through the hole 54 at the circle 56, and the width of the waist 59 is such that the boss 40 cannot slide into the ellipse 58 portion of the hole 54. The boss 40 does not contact the leg 20 of the patient.

The transmitting coil 18 is now positioned close to the leg 20 of the patient, and is separated from the leg 20 of the patient by the plate 48.

The hole 62 in the mating mounting pad 24 allows water to drain from the mounting 10 so that the adhesive (not shown) is not dissolved too quickly on bathing or showering.

Rotational movement of the transmitting coil housing 22 relative to the mating mounting pad 24 is possible, since the cylindrical boss 40 is free to rotate within the hole 54.

Once the transmitting coil 18 has been mounted to the leg 20 in this way and the heel sensor 10 has been placed under the heel 12 (for example in a shoe (not shown)), the foot-drop treatment unit may be used. Pressure and lack of pressure of the heel 12 on the floor (not shown) are detected using the heel sensor 10. This information is communicated to the control unit 14 via the radio link. The control unit 14 performs analysis on the information from the heel sensor 10 to detect when the patient wishes to step forward. At these times, a signal is sent from the control unit 14 to the magnetic transmitting coil 18 via the wire 28. The magnetic transmitting coil 18 produces a magnetic signal in response. This magnetic signal passes through the skin of the leg 20 and causes the stimulator 26 to produce a stimulating signal (not shown) at the stimulation electrode 30. This stimulating signal causes the dorsiflexor muscles in the leg 20 to contract, dorsiflexing the foot of the patient to enable a step forward to be taken.

The preferred embodiment of the present invention has several advantages over conventional foot-drop treatment unit mountings. First, the magnetic coil housing 22 can be mounted to the mounting pad 24 with one hand. This may be particularly important for patients who also suffer from upper body paralysis. Secondly, the magnetic coil housing 22 can be manipulated through clothing during mounting to the mounting pad 24. Thirdly, the magnetic coil housing 22 is rotatable on the mounting pad 24, in contrast to the conventional Velcro® pad. This has the advantage that the coil housing 22 may be adjusted after fastening. The coil housing 22 will also rotate under torsional force from the wire 28 which connects the coil to the control unit 14, to prevent a twisted wire 28 or inadvertent disconnection of the magnetic coil housing 22. Fourthly, whereas a Velcro® attachment will form even if the two pads are substantially misaligned (provided there is some overlap), the proposed mounting accurately locates the coil at the desired place. This facilitates precise mounting of the coil even when the mounting 10 is not in sight, for example when it is hidden under clothing.

Whilst the invention has been described with reference to the illustrated preferred embodiment, it will be recognised that various modifications are possible within the scope of the invention.

For example, the transmitting coil mounting 21 of the invention has been described in the context of a foot-drop treatment unit. However, the transmitting or receiving coil mounting 21 might be used in a variety of devices, for example to stimulate other types of muscle contraction (e.g. heart contraction in a pacemaker), to interrogate a subcutaneous sensor, or to stimulate drug release from an implant.

What is claimed is:

1. A transmitter apparatus, comprising:
   a controller;
   a transmitter;
   a wire connecting the controller to the transmitter; and
   a mounting for fixing the transmitter to a surface, the mounting comprising a mounting pad and a transmitter housing, the mounting pad having a face for applying to the surface and an opposite face and being provided with a first mating component of a rotatable connection and the transmitter housing having a second cooperating mating component of the rotatable connection, whereby the two components are mateable to mount the transmitter housing rotatably on the opposite face of the mounting pad;
   wherein a housing rotatable relative to the mounting pad is provided while the two components are mated; and
   wherein the rotatable connection is attachable and detachable by the user.

2. A transmitter apparatus as claimed in claim 1, wherein the transmitter is a transmitting antenna.

3. A transmitter apparatus as claimed in claim 2, wherein the transmitting antenna is a transmitting coil.

4. A transmitter apparatus as claimed in claim 3, wherein the transmitting coil is a magnetic coil or an aerial coil.

5. A transmitter apparatus as claimed in claim 1, wherein the face of the mounting pad for applying to the surface is an adhesive face.

6. A transmitter apparatus as claimed in claim 1, wherein the mounting pad is provided with an adhesive tape extending beyond the mounting pad for fixing the mounting pad to the surface.

7. A transmitter apparatus as claimed in claim 1, wherein the transmitter housing is in the form of a dish and the mounting pad is in the form of a plate, such that when the two components are mated the mounting pad sits at least substantially within the transmitter housing.

8. A transmitter apparatus as claimed in claim 1, wherein the one of the first and second mating components of the mounting is a flanged boss and the other of the first and second mating components is a cooperating hole.

9. A transmitter apparatus as claimed in claim 8, wherein the cooperating hole has a first portion through which the flanged boss can pass and a second portion within which the flanged boss can sit but through which the flanged boss cannot pass.

10. A transmitter apparatus as claimed in claim 9, wherein the first portion and the second portion of the cooperating hole are divided by a flexible waist through which the flanged boss can be urged.

11. An electrical stimulation unit comprising a sensor, a transmitter apparatus as claimed in claim 1 and a stimulator, wherein the sensor controls the transmitter by means of the controller to transmit a signal to the stimulator.

12. An electrical stimulation unit as claimed in claim 11 for the treatment of foot-drop, wherein the sensor is a pressure sensor for placing on the heel and the stimulator is a stimulator for the peroneal nerve.

13. A method of producing nerve stimulation using an electrical stimulation unit as claimed in claim 11, comprising:
   the sensor detecting a stimulus;
   the sensor transmitting a signal to the controller;
   the controller controlling the transmitter to transmit a signal to the stimulator; and
   the stimulator producing nerve stimulation.

14. A transmitter apparatus as claimed in claim 1, wherein the transmitter is a transmitter for controlling an electrical nerve stimulator.

15. A transmitter apparatus as claimed in claim 14, wherein the electrical nerve stimulator is implantable.

16. A transmitter apparatus as claimed in claim 1, wherein the wire connecting the controller to the transmitter runs external to the transmitter housing.

* * * * *